United States Patent
Schmidt et al.

(10) Patent No.: US 7,576,973 B2
(45) Date of Patent: Aug. 18, 2009

(54) CONFIGURATIONS AND METHODS FOR MAKING CAPACITOR CONNECTIONS

(75) Inventors: Brian L. Schmidt, Forest Lake, MN (US); Michael J. O'Phelan, Oakdale, MN (US); James M. Poplett, Plymouth, MN (US); Robert R. Tong, Valencia, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/904,285

(22) Filed: Sep. 26, 2007

(65) Prior Publication Data

US 2008/0030928 A1   Feb. 7, 2008

Related U.S. Application Data

(62) Division of application No. 09/706,576, filed on Nov. 3, 2000, now Pat. No. 7,355,841.

(51) Int. Cl.
  *H01G 9/10* (2006.01)
  *H01G 9/08* (2006.01)
  *H01G 2/10* (2006.01)
(52) U.S. Cl. ..................... 361/520; 361/517
(58) Field of Classification Search .............. 361/523, 361/517, 520
  See application file for complete search history.

(56) References Cited

U.S. PATENT DOCUMENTS

| 1,474,486 | A | * | 11/1923 | MacPherson | 361/329 |
|---|---|---|---|---|---|
| 2,555,326 | A | | 6/1951 | Doughty, Jr. | |
| 3,150,301 | A | | 9/1964 | Schils et al. | |
| 3,389,311 | A | | 6/1968 | Rayno | |
| 3,424,857 | A | | 1/1969 | Miller et al. | |
| 3,611,055 | A | * | 10/1971 | Zeppieri et al. | 361/523 |
| 3,686,535 | A | | 8/1972 | Piper | |

(Continued)

FOREIGN PATENT DOCUMENTS

EP   0224733 A1   6/1987

(Continued)

OTHER PUBLICATIONS

U.S. Appl. No. 09/705,976, Non Final Office Action mailed Apr. 1, 2002, 14 pgs.

(Continued)

*Primary Examiner*—Eric Thomas
*Assistant Examiner*—David M Sinclair
(74) *Attorney, Agent, or Firm*—Schwegman, Lundberg & Woessner, P.A.

(57) ABSTRACT

An exemplary capacitor has a capacitor stack positioned in a case with a conductor positioned between the case and a lid. In one embodiment the conductor is positioned between the lid and an upper rim of the case and is welded to the lid and case. In one aspect, a capacitor constructed with round wire connectors for interconnecting anode and cathode layers. In one aspect, a configuration for electrically connecting a terminal wire to a capacitor case in which an end of the wire is attached to the case in end-on fashion. The terminal wire may have an expanded end for attaching to the capacitor case in a manner that minimizes the effect on the height profile of the case.

18 Claims, 7 Drawing Sheets

U.S. PATENT DOCUMENTS

| | | | |
|---|---|---|---|
| 3,686,538 A | 8/1972 | Webster | |
| 3,803,457 A | 4/1974 | Yamamoto | |
| 3,828,227 A | 8/1974 | Millard et al. | |
| 3,859,574 A | 1/1975 | Brazier | |
| 3,938,228 A * | 2/1976 | Kemkers et al. | 29/25.42 |
| 3,993,508 A | 11/1976 | Erlichman | |
| 4,045,644 A | 8/1977 | Shafer et al. | |
| 4,047,790 A | 9/1977 | Carino | |
| 4,086,148 A | 4/1978 | Badia | |
| 4,113,921 A | 9/1978 | Goldstein et al. | |
| 4,131,935 A | 12/1978 | Clement | |
| 4,169,003 A | 9/1979 | Dangel et al. | |
| 4,171,477 A | 10/1979 | Funari | |
| 4,232,099 A | 11/1980 | Sullivan | |
| 4,247,883 A | 1/1981 | Thompson et al. | |
| 4,267,565 A | 5/1981 | Puppolo et al. | |
| 4,307,142 A | 12/1981 | Blitstein et al. | |
| 4,394,713 A | 7/1983 | Yoshida | |
| 4,425,412 A | 1/1984 | Dittmann et al. | |
| 4,481,083 A | 11/1984 | Ball et al. | |
| 4,553,304 A | 11/1985 | Fleuret | |
| 4,571,662 A | 2/1986 | Conquest et al. | |
| 4,659,636 A | 4/1987 | Suzuki et al. | |
| 4,683,516 A | 7/1987 | Miller | |
| 4,745,039 A | 5/1988 | Yoshinaka | |
| 4,931,899 A | 6/1990 | Pruett | |
| 5,041,942 A | 8/1991 | Carrico | |
| 5,131,388 A | 7/1992 | Pless et al. | |
| 5,173,375 A | 12/1992 | Cretzmeyer et al. | |
| 5,175,067 A | 12/1992 | Taylor et al. | |
| 5,306,581 A | 4/1994 | Taylor et al. | |
| 5,333,095 A | 7/1994 | Stevenson et al. | |
| 5,377,073 A | 12/1994 | Fukaumi et al. | |
| 5,422,200 A | 6/1995 | Hope et al. | |
| 5,439,760 A | 8/1995 | Howard et al. | |
| 5,507,966 A | 4/1996 | Liu | |
| 5,522,851 A | 6/1996 | Fayram | |
| 5,527,346 A | 6/1996 | Kroll | |
| 5,554,178 A | 9/1996 | Dahl et al. | |
| 5,584,890 A | 12/1996 | MacFarlane et al. | |
| 5,628,801 A | 5/1997 | MacFarlane et al. | |
| 5,634,938 A | 6/1997 | Swanson et al. | |
| 5,640,756 A | 6/1997 | Brown et al. | |
| 5,658,319 A | 8/1997 | Kroll | |
| 5,660,737 A | 8/1997 | Elias et al. | |
| 5,691,079 A | 11/1997 | Daugaard | |
| 5,716,729 A | 2/1998 | Sunderland et al. | |
| 5,734,546 A * | 3/1998 | Kuriyama et al. | 361/523 |
| 5,754,394 A * | 5/1998 | Evans et al. | 361/516 |
| 5,774,261 A | 6/1998 | Omori et al. | |
| 5,776,632 A | 7/1998 | Honegger | |
| 5,779,699 A | 7/1998 | Lipson | |
| 5,800,724 A | 9/1998 | Habeger et al. | |
| 5,801,917 A | 9/1998 | Elias | |
| 5,811,206 A | 9/1998 | Sunderland et al. | |
| 5,814,082 A | 9/1998 | Fayram et al. | |
| 5,867,363 A | 2/1999 | Tsai et al. | |
| 5,882,362 A | 3/1999 | Muffoletto et al. | |
| 5,901,867 A | 5/1999 | Mattson | |
| 5,908,151 A | 6/1999 | Elias | |
| 5,922,215 A | 7/1999 | Pless et al. | |
| 5,926,357 A | 7/1999 | Elias et al. | |
| 5,926,362 A | 7/1999 | Muffoletto et al. | |
| 5,930,109 A | 7/1999 | Fishler | |
| 5,949,638 A | 9/1999 | Greenwood, Jr. et al. | |
| 5,950,131 A | 9/1999 | Vilmur | |
| 5,963,418 A | 10/1999 | Greenwood, Jr. et al. | |
| 5,968,210 A | 10/1999 | Strange et al. | |
| 5,973,906 A | 10/1999 | Stevenson et al. | |
| 5,983,472 A | 11/1999 | Fayram et al. | |
| 6,002,969 A | 12/1999 | Machek et al. | |
| 6,004,692 A | 12/1999 | Muffoletto et al. | |
| 6,006,133 A | 12/1999 | Lessar et al. | |
| 6,009,348 A | 12/1999 | Rorvick et al. | |
| 6,030,480 A | 2/2000 | Face, Jr. et al. | |
| 6,032,075 A | 2/2000 | Pignato et al. | |
| 6,040,082 A | 3/2000 | Haas et al. | |
| 6,042,624 A | 3/2000 | Breyen et al. | |
| 6,052,625 A | 4/2000 | Marshall | |
| 6,094,788 A | 8/2000 | Farahmandi et al. | |
| 6,099,600 A | 8/2000 | Yan et al. | |
| 6,104,961 A | 8/2000 | Conger et al. | |
| 6,110,233 A | 8/2000 | O'Phelan et al. | |
| 6,110,321 A | 8/2000 | Day et al. | |
| 6,117,194 A | 9/2000 | Strange et al. | |
| 6,118,651 A | 9/2000 | Mehrotra et al. | |
| 6,139,986 A | 10/2000 | Kurokawa et al. | |
| 6,141,205 A | 10/2000 | Nutzman et al. | |
| 6,157,531 A | 12/2000 | Breyen et al. | |
| 6,162,264 A | 12/2000 | Miyazaki et al. | |
| 6,184,160 B1 | 2/2001 | Yan et al. | |
| 6,191,931 B1 | 2/2001 | Paspa et al. | |
| 6,225,778 B1 | 5/2001 | Hayama et al. | |
| 6,249,423 B1 | 6/2001 | O'Phelan et al. | |
| 6,249,709 B1 | 6/2001 | Conger et al. | |
| 6,256,542 B1 | 7/2001 | Marshall et al. | |
| 6,259,954 B1 | 7/2001 | Conger et al. | |
| 6,275,372 B1 | 8/2001 | Vassallo et al. | |
| 6,275,729 B1 | 8/2001 | O'Phelan et al. | |
| 6,283,985 B1 | 9/2001 | Harguth et al. | |
| 6,324,049 B1 | 11/2001 | Inagawa et al. | |
| 6,326,587 B1 | 12/2001 | Cardineau et al. | |
| 6,330,925 B1 | 12/2001 | Ovshinsky et al. | |
| 6,375,688 B1 | 4/2002 | Akami et al. | |
| 6,380,577 B1 | 4/2002 | Cadwallader | |
| 6,388,866 B1 | 5/2002 | Rorvick et al. | |
| 6,402,793 B1 * | 6/2002 | Miltich et al. | 361/520 |
| 6,404,619 B1 | 6/2002 | Marshall et al. | |
| 6,409,776 B1 | 6/2002 | Yan et al. | |
| 6,413,283 B1 | 7/2002 | Day et al. | |
| 6,442,015 B1 | 8/2002 | Niiori et al. | |
| 6,451,073 B1 | 9/2002 | Farahmandi et al. | |
| 6,459,566 B1 | 10/2002 | Casby et al. | |
| 6,493,212 B1 | 12/2002 | Clarke et al. | |
| 6,509,588 B1 | 1/2003 | O'Phelan et al. | |
| 6,522,525 B1 | 2/2003 | O'Phelan et al. | |
| 6,556,863 B1 | 4/2003 | O'Phelan et al. | |
| 6,571,126 B1 | 5/2003 | O'Phelan et al. | |
| 6,585,152 B2 | 7/2003 | Farahmandi et al. | |
| 6,628,505 B1 | 9/2003 | Andelman | |
| 6,674,634 B2 | 1/2004 | O'Phelan et al. | |
| 6,684,102 B1 | 1/2004 | O'Phelan et al. | |
| 6,687,118 B1 | 2/2004 | O'Phelan et al. | |
| 6,699,265 B1 | 3/2004 | O'Phelan et al. | |
| 6,709,946 B2 | 3/2004 | O'Phelan et al. | |
| 6,763,265 B2 | 7/2004 | O'Phelan et al. | |
| 6,795,729 B1 | 9/2004 | Breyen et al. | |
| 6,833,987 B1 | 12/2004 | O'Phelan | |
| 6,885,548 B2 | 4/2005 | Nyberg | |
| 6,885,887 B2 | 4/2005 | O'Phelan et al. | |
| 6,957,103 B2 | 10/2005 | Schmidt et al. | |
| 6,985,351 B2 | 1/2006 | O'Phelan et al. | |
| 6,990,375 B2 | 1/2006 | Kloss et al. | |
| 6,999,304 B2 | 2/2006 | Schmidt et al. | |
| 7,072,713 B2 | 7/2006 | O'Phelan et al. | |
| 7,079,897 B2 | 7/2006 | Sun et al. | |
| 7,107,099 B1 | 9/2006 | O'Phelan et al. | |
| 7,120,008 B2 | 10/2006 | Sherwood | |
| 7,154,739 B2 | 12/2006 | O'Phelan | |
| 7,157,671 B2 | 1/2007 | O'Phelan et al. | |
| 7,177,692 B2 | 2/2007 | O'Phelan et al. | |
| 7,180,727 B2 | 2/2007 | Poplett | |
| 7,190,569 B2 | 3/2007 | O'Phelan et al. | |
| 7,190,570 B2 | 3/2007 | Schmidt et al. | |

| | | |
|---|---|---|
| 7,221,556 B2 | 5/2007 | Schmidt et al. |
| 7,347,880 B2 | 3/2008 | O'Phelan et al. |
| 7,355,841 B1 | 4/2008 | Schmidt et al. |
| 7,365,960 B2 | 4/2008 | O'Phelan et al. |
| 7,456,077 B2 | 11/2008 | Sherwood et al. |
| 7,479,349 B2 | 1/2009 | O'Phelan et al. |
| 2001/0020319 A1 | 9/2001 | Farahmandi et al. |
| 2003/0077509 A1 | 4/2003 | Probst et al. |
| 2003/0165744 A1 | 9/2003 | Schubert et al. |
| 2003/0195568 A1 | 10/2003 | O'Phelan et al. |
| 2004/0019268 A1 | 1/2004 | Schmidt et al. |
| 2004/0114311 A1 | 6/2004 | O'Phelan et al. |
| 2004/0127952 A1 | 7/2004 | O'Phelan et al. |
| 2004/0147961 A1 | 7/2004 | O'Phelan et al. |
| 2004/0173835 A1 | 9/2004 | Schmidt et al. |
| 2004/0174658 A1 | 9/2004 | O'Phelan et al. |
| 2004/0193221 A1 | 9/2004 | O'Phelan et al. |
| 2004/0215281 A1 | 10/2004 | O'Phelan et al. |
| 2005/0010253 A1 | 1/2005 | O'Phelan et al. |
| 2005/0017888 A1 | 1/2005 | Sherwood et al. |
| 2005/0052825 A1 | 3/2005 | O'Phelan et al. |
| 2005/0221171 A1 | 10/2005 | Haasl et al. |
| 2006/0009808 A1 | 1/2006 | Schmidt et al. |
| 2006/0012942 A1 | 1/2006 | Poplett |
| 2006/0107506 A1 | 5/2006 | Doffing et al. |
| 2006/0152887 A1 | 7/2006 | Schmidt et al. |
| 2006/0174463 A1 | 8/2006 | O'Phelan et al. |
| 2006/0247715 A1 | 11/2006 | Youker |
| 2006/0257726 A1 | 11/2006 | Kelley et al. |
| 2007/0118182 A1 | 5/2007 | O'Phelan et al. |

FOREIGN PATENT DOCUMENTS

| | | |
|---|---|---|
| EP | 0019470 A1 | 4/2000 |
| GB | 825900 | 12/1959 |
| GB | 2132019 | 6/1984 |
| JP | 52-004051 | 1/1977 |
| JP | 59-083772 | 5/1984 |
| JP | 05-074664 | 3/1993 |
| WO | WO-98/27562 A1 | 6/1998 |
| WO | WO-99/51302 | 10/1999 |
| WO | WO-9951302 A1 | 10/1999 |
| WO | WO-00/19470 | 4/2000 |
| WO | WO-00/19470 A1 | 4/2000 |
| WO | WO-0019470 A1 | 4/2000 |
| WO | WO-02/37515 A2 | 5/2002 |
| WO | WO-2006/002148 A1 | 1/2006 |
| WO | WO-2006002148 A1 | 1/2006 |

OTHER PUBLICATIONS

U.S. Appl. No. 09/705,976, Notice of Allowance mailed Aug. 6, 2002, 6 pgs.
U.S. Appl. No. 09/705,976 Response filed Jul. 1, 2002 to Non Final Office Action mailed Apr. 1, 2002, 8 pgs.
U.S. Appl. No. 09/705,994, Non Final Office Action mailed Sep. 11, 2002, 8 pgs.
U.S. Appl. No. 09/705,994, Notice of Allowance mailed Dec. 26, 2002, 7 pgs.
U.S. Appl. No. 09/705,994, Response filed Dec. 10, 2002 to Non Final Office Action mailed Sep. 11, 2002, 4 pgs.
U.S. Appl. No. 09/706,447, Non Final Office Action mailed Mar. 26, 2003, 9 pgs.
U.S. Appl. No. 09/706,447, Notice of Allowance mailed Sep. 23, 2003, 6 pgs.
U.S. Appl. No. 09/706,447, Response filed Jun. 25, 2003 to Non Final Office Action mailed Mar. 26, 2003, 10 pgs.
U.S. Appl. No. 09/706,515, Non Final Office Action mailed Mar. 21, 2003, 12 pgs.
U.S. Appl. No. 09/706,515, Notice of Allowance mailed Aug. 13, 2003, 12 pgs.
U.S. Appl. No. 09/706,515, Response filed Jun. 23, 2003 to Non Final Office Action mailed Mar. 21, 2003, 11 pgs.
U.S. Appl. No. 09/706,517, Non Final Office Action mailed Apr. 23, 2003, 15 pgs.
U.S. Appl. No. 09/706,517, Non Final Office Action mailed Dec. 15, 2003, 10 pgs.
U.S. Appl. No. 09/706,517, Notice of Allowance mailed Jul. 1, 2004, 8 pgs.
U.S. Appl. No. 09/706,517, Response filed Mar. 15, 2004 to Non Final Office Action mailed Dec. 15, 2003, 11 pgs.
U.S. Appl. No. 09/706,517, Response filed Aug. 25, 2003 to Non Final Office Action mailed Apr. 23, 2003, 13 pgs.
U.S. Appl. No. 09/706,518, Non Final Office Action mailed Mar. 24, 2003, 9 pgs.
U.S. Appl. No. 09/706,518, Non Final Office Action mailed Apr. 18, 2002, 13 pgs.
U.S. Appl. No. 09/706,518, Non Final Office Action mailed Oct. 4, 2002, 9 pgs.
U.S. Appl. No. 09/706,518, Notice of Allowance mailed Sep. 9, 2003, 10 pgs.
U.S. Appl. No. 09/706,518, Response filed Jan. 6, 2003 to Non Final Office Action mailed Oct. 4, 2002, 4 pgs.
U.S. Appl. No. 09/706,518, Response filed Jun. 24, 2003 to Non Final Office Action mailed Mar. 24, 2003, 9 pgs.
U.S. Appl. No. 09/706,518, Response filed Jul. 18, 2002 to Non Final Office Action mailed Apr. 18, 2002, 7 pgs.
U.S. Appl. No. 09/706,519, Non Final Office Action mailed Apr. 24, 2002, 8 pgs.
U.S. Appl. No. 09/706,519, Notice of Allowance mailed Aug. 26, 2002, 9 pgs.
U.S. Appl. No. 09/706,519, Response filed Jul. 24, 2002 to Non Final Office Action mailed Apr. 24, 2002, 4 pgs.
U.S. Appl. No. 09/706,576, Amendment and Response filed Jun. 12, 2003 to Notice of Non-Compliant Amendment mailed May 12, 2003, 12 pgs.
U.S. Appl. No. 09/706,576, Notice of Non-Compliant Amendment mailed May 12, 2003, 2 pgs.
U.S. Appl. No. 09/706,576, Amendment and Response filed Oct. 12, 2004 to Final Office Action mailed Sep. 10, 2003, 10 pgs.
U.S. Appl. No. 09/706,576, Final Office Action mailed Sep. 10, 2003, 6 pgs.
U.S. Appl. No. 09/706,576, Final Office Action mailed Oct. 5, 2005, 13 pgs.
U.S. Appl. No. 09/706,576, Non Final Office Action mailed Jan. 10, 2005, 12 pgs.
U.S. Appl. No. 09/706,576, Non Final Office Action mailed Feb. 2, 2007, 7 pgs.
U.S. Appl. No. 09/706,576, Non Final Office Action mailed Oct. 31, 2002, 8 pgs.
U.S. Appl. No. 09/706,576, Notice of Allowance mailed Jul. 18, 2007, 5 pgs.
U.S. Appl. No. 09/706,576, Supplemental Notice of Allowability mailed Sep. 6, 2007, 4 pgs.
U.S. Appl. No. 09/706,576, Response filed Apr. 30, 2003 to Non Final Office Action mailed Oct. 31, 2002, 12 pgs.
U.S. Appl. No. 09/706,576, Response filed Jul. 2, 2007 to Non Final Office Action mailed Feb. 2, 2007, 5 pgs.
U.S. Appl. No. 09/706,576, Response filed Jul. 11, 2005 to Non Final Office Action mailed Jan. 10, 2005, 12 pgs.
U.S. Appl. No. 09/706,576, Response filed Nov. 6, 2006 to Final Office Action mailed Oct. 5, 2005, 6 pgs.
U.S. Appl. No. 09/706,579, Non Final Office Action mailed Mar. 7, 2003, 9 pgs.
U.S. Appl. No. 09/706,579, Non Final Office Action mailed Oct. 3, 2003, 7 pgs.
U.S. Appl. No. 09/706,579, Notice of Allowance mailed Feb. 4, 2004, 5 pgs.
U.S. Appl. No. 09/706,579, Notice of Allowance mailed Mar. 4, 2005, 21 pgs.
U.S. Appl. No. 09/706,579, Notice of Allowance mailed Apr. 6, 2006, 17 pgs.
U.S. Appl. No. 09/706,579, Notice of Allowance mailed Sep. 9, 2005, 9 pgs.
U.S. Appl. No. 09/706,579, Response filed Jul. 7, 2003 to Non Final Office Action mailed Mar. 7, 2003, 9 pgs.

U.S. Appl. No. 09/706,579, Response filed Dec. 30, 2003 to Non Final Office Action mailed Oct. 3, 2003, 9 pgs.
U.S. Appl. No. 10/287,285, Non Final Office Action mailed Feb. 27, 2003, 12 pgs.
U.S. Appl. No. 10/287,285, Notice of Allowance mailed Aug. 4, 2003, 10 pgs.
U.S. Appl. No. 10/287,285, Response filed Jun. 27, 2003 to Non Final Office Action mailed Feb. 27, 2003, 11 pgs.
U.S. Appl. No. 10/299,234, Notice of Allowance mailed Sep. 25, 2003, 9 pgs.
U.S. Appl. No. 10/299,234, Preliminary Amendment filed Nov. 19, 2002, 2 pgs.
U.S. Appl. No. 11/413,680, Non Final Office Action mailed May 21, 2004, 6 pgs.
U.S. Appl. No. 11/413,680, Non Final Office Action mailed Nov. 18, 2004, 11 pgs.
U.S. Appl. No. 11/413,680, Notice of Allowance mailed May 3, 2005, 5 pgs.
U.S. Appl. No. 11/413,680, Response filed Feb. 18, 2005 to Non Final Office Action mailed Nov. 18, 2004, 9 pgs.
U.S. Appl. No. 11/413,680, Response filed Aug. 23, 2004 to Non Final Office Action mailed May 21, 2004, 9 pgs.
U.S. Appl. No. 11/418,616, Non Final Office Action mailed Aug. 12, 2003, 7 pgs.
U.S. Appl. No. 11/418,616, Notice of Allowance mailed Feb. 27, 2004, 6 pgs.
U.S. Appl. No. 11/418,616, Response filed Feb. 12, 2004 to Non Final Office Action mailed Aug. 12, 2003, 7 pgs.
U.S. Appl. No. 10/729,424, Non Final Office Action mailed Oct. 4, 2004, 25 pgs.
U.S. Appl. No. 10/729,424, Notice of Allowance mailed Feb. 4, 2005, 7 pgs.
U.S. Appl. No. 10/729,424, Response filed Jan. 4, 2005 to Non Final Office Action mailed Oct. 4, 2004, 10 pgs.
U.S. Appl. No. 10/736,209, Final Office Action mailed Aug. 25, 2005, 11 pgs.
U.S. Appl. No. 10/736,209, Non Final Office Action mailed Mar. 8, 2005, 13 pgs.
U.S. Appl. No. 10/736,209, Non Final Office Action mailed Mar. 13, 2005, 12 pgs.
U.S. Appl. No. 10/736,209, Notice of Allowance mailed Nov. 2, 2006, 10 pgs.
U.S. Appl. No. 10/736,209, Response filed Jun. 8, 2005 to Non Final Office Action mailed Mar. 8, 2005, 9 pgs.
U.S. Appl. No. 10/736,209, Response filed Aug. 14, 2006 to Non Final Office Action mailed Mar. 13, 2006, 10 pgs.
U.S. Appl. No. 10/736,209, Response filed Dec. 23, 2005 to Final Office Action mailed Aug. 25, 2005, 8 pgs.
U.S. Appl. No. 10/758,677, Final Office Action mailed May 17, 2006, 7 pgs.
U.S. Appl. No. 10/758,677, Non Final Office Action mailed Feb. 9, 2005, 5 pgs.
U.S. Appl. No. 10/758,677, Non Final Office Action mailed Jul. 13, 2004, 12 pgs.
U.S. Appl. No. 10/758,677, Non Final Office Action mailed Nov. 16, 2005, 5 pgs.
U.S. Appl. No. 10/758,677, Notice of Allowance mailed Aug. 24, 2006, 16 pgs.
U.S. Appl. No. 10/758,677, Response filed Feb. 16, 2006 to Non Final Office Action mailed Nov. 16, 2005, 9 pgs.
U.S. Appl. No. 10/758,677, Response filed Jul. 17, 2006 to Final Office Action mailed May 17, 2006, 9 pgs.
U.S. Appl. No. 10/758,677, Response filed Aug. 9, 2005 to Non Final Office Action mailed Feb. 9, 2005, 9 pgs.
U.S. Appl. No. 10/758,677, Response filed Nov. 15, 2004 to Non Final Office Action mailed Jul. 13, 2004, 9 pgs.
U.S. Appl. No. 10/758,701, Non Final Office Action mailed Aug. 9, 2005, 7 pgs.
U.S. Appl. No. 10/758,701, Notice of Allowance mailed Jan. 25, 2006, 7 pgs.
U.S. Appl. No. 10/758,701, Response filed Nov. 9, 2005 to Non Final Office Action mailed Aug. 9, 2005, 8 pgs.
U.S. Appl. No. 10/804,288, Notice of Allowance mailed Aug. 23, 2005, 24 pgs.
U.S. Appl. No. 10/804,288, Preliminary Amendment filed Mar. 18, 2004, 5 pgs.
U.S. Appl. No. 10/846,805, Non Final Office Action mailed Apr. 19, 2006, 14 pgs.
U.S. Appl. No. 10/846,805, Notice of Allowance mailed Sep. 27, 2006, 7 pgs.
U.S. Appl. No. 10/846,805, Preliminary Amendment filed May 14, 2004, 6 pgs.
U.S. Appl. No. 10/846,805, Response filed Jul. 19, 2006 to Non Final Office Action mailed Apr. 19, 2006, 8 pgs.
U.S. Appl. No. 10/882,144, Notice of Allowance mailed Dec. 14, 2004, 12 pgs.
U.S. Appl. No. 10/969,441, Non Final Office Action mailed Apr. 1, 2005, 13 pgs.
U.S. Appl. No. 10/969,441, Non Final Office Action mailed Sep. 19, 2005, 8 pgs.
U.S. Appl. No. 10/969,441, Notice of Allowance mailed Mar. 29, 2006, 8 pgs.
U.S. Appl. No. 10/969,441, Notice of Allowance mailed Sep. 11, 2006, 8 pgs.
U.S. Appl. No. 10/969,441, Response filed Jun. 29, 2005 to Non Final Office Action mailed Apr. 1, 2005, 7 pgs.
U.S. Appl. No. 10/969,441, Response filed Dec. 19, 2005 to Non Final Office Action mailed Sep. 19, 2005, 8 pgs.
U.S. Appl. No. 11/226,954, Non Final Office Action mailed May 17, 2006, 13 pgs.
U.S. Appl. No. 11/226,954, Non Final Office Action mailed Dec. 15, 2005, 18 pgs.
U.S. Appl. No. 11/226,954, Notice of Allowance mailed Nov. 1, 2006, 5 pgs.
U.S. Appl. No. 11/226,954, Response filed Mar. 15, 2006 to Non Final Office Action mailed Dec. 15, 2005, 12 pgs.
U.S. Appl. No. 11/226,954, Response filed Aug. 17, 2006 to Non Final Office Action mailed May 17, 2006, 8 pgs.
U.S. Appl. No. 11/325,931, Non Final Office Action mailed Jul. 21, 2006, 7 pgs.
U.S. Appl. No. 11/325,931, Notice of Allowance mailed Jan. 16, 2007, 15 pgs.
U.S. Appl. No. 11/325,931, Response filed Oct. 23, 2006 to Non Final Office Action mailed Jul. 21, 2006, 9 pgs.
U.S. Appl. No. 11/668,109, Non Final Office Action mailed Jun. 27, 2007, 13 pgs.
PCT Application No. PCT/US01/45202, International Search Report mailed Feb. 21, 2003, 6 pgs.
PCT Application No. PCT/US01/50257, International Search Report mailed Jun. 4, 2003, 6 pgs.
PCT Application No. PCT/US2005.021898, International Preliminary Report on Patentability mailed Jan. 11, 2007, 7 pgs.
PCT Application No. PCT/US2005/021898, International Search Report mailed Mar. 11, 2005, 4 pgs.
"U.S. Appl. No. 10/874,798 Advisory Action mailed Jan. 8, 2008", 3 pgs.
"U.S. Appl. No. 10/360,551 Notice of Allowance mailed Sep. 11, 2008", 6 pgs.
"U.S. Appl. No. 10/874,798 Notice of Allowance mailed Jul. 24, 2008", 4 pgs.
Kelley, Shawn, et al., "Method and Apparatus for Porous Insulative Film for Insulating Energy Source Layers", U.S. Appl. No. 11/127,025, filed May 11, 2005, 21 pages.

* cited by examiner

CONFIGURATIONS AND METHODS FOR MAKING CAPACITOR CONNECTIONS

CROSS-REFERENCE TO RELATED APPLICATIONS

This application is a divisional of U.S. patent application Ser. No. 09/706,576, filed on Nov. 3, 2000, now issued as U.S. Pat. No. 7,355,841, the specification of which is incorporated herein by reference.

This application is related to U.S. patent application Ser. No. 11/226,954, filed on Sep. 15, 2005, entitled CONFIGURATIONS AND METHODS FOR MAKING CAPACITOR CONNECTIONS, now issued as U.S. Pat. No. 7,190,570; U.S. patent application Ser. No. 10/413,680, filed on Apr. 15, 2003, entitled CONFIGURATIONS AND METHODS FOR MAKING CAPACITOR CONNECTIONS, now issued as U.S. Pat. No. 6,957,103; and U.S. patent application Ser. No. 09/706,447, filed on Nov. 3, 2000, entitled FLAT CAPACITOR FOR AN IMPLANTABLE MEDICAL DEVICE, now issued as U.S. Pat. No. 6,699,265, the specification of which is incorporated herein by reference.

TECHNICAL FIELD

The present invention concerns implantable medical devices, such as defibrillators and cardioverters, particularly structures and methods for capacitors in such devices.

BACKGROUND

Since the early 1980s, thousands of patients prone to irregular and sometimes life-threatening heart rhythms have had miniature heart monitors, particularly defibrillators and cardioverters, implanted in their bodies. These devices detect onset of abnormal heart rhythms and automatically apply corrective electrical therapy, specifically one or more bursts of electric current, to hearts. When the bursts of electric current are properly sized and timed, they restore normal heart function without human intervention, sparing patients considerable discomfort and often saving their lives.

The typical defibrillator or cardioverter includes a set of electrical leads, which extend from a sealed housing into the walls of a heart after implantation. Within the housing are a battery for supplying power, monitoring circuitry for detecting abnormal heart rhythms, and a capacitor for delivering bursts of electric current through the leads to the heart.

The capacitor may take the form of a flat aluminum electrolytic capacitor. This type of capacitor generally includes a stack of flat capacitive elements, with each capacitive element including a paper separator between two sheets of aluminum foil. The aluminum foil layers are divided into a group of anode layers and a group of cathode layers.

The anodes and the cathodes of the capacitor elements are connected together to provide a total capacitance. After being connected, the respective anodes and cathodes are connected to terminals for being coupled to circuitry outside the capacitor case. These internal and external connections can be time-consuming to make and can take up valuable space both within and outside the capacitor.

Since defibrillators and cardioverters are typically implanted in the left region of the chest or in the abdomen, a smaller size device, which is still capable of delivering the required level of electrical energy, is desirable.

Accordingly, there is a need for capacitor structures and methods of manufacture which provide greater process control, less expensive manufacturing, provide for a design efficiently utilizing space within the capacitor case, and provide for a compact capacitor design capable of providing the required pulse of energy for use within the implantable device.

SUMMARY

To address these needs, capacitor structures and assembly methods have been devised. One capacitor has a capacitor stack positioned in a case with a cathode conductor positioned between a cover and the case. In one embodiment, an anode conductor is positioned between the cover and the case. In one embodiment a cathode conductor is positioned between the cover and an upper rim of the case and is welded to the cover and case. One or more of these embodiments provide an arrangement which reduces the space required for connecting and routing the cathode conductor and thus allows a reduction in the size of the capacitor, or alternatively an increase in its energy storage capacity.

One aspect provides a capacitor having a capacitor terminal wire which is electrically connected to a capacitor case by welding or brazing an end of the wire to the case in an end-on fashion. In one embodiment, the end of the wire is expanded so as to be, for example, in the shape of a nailhead. The expanded end presents sufficient surface area to enable a mechanically stable connection while minimizing the size of the footprint of the case within the housing of an implantable medical device.

One aspect provides interconnections between anode and cathode layers which are made by round wire connectors that are attached to the individual anode and cathode layers. The anode layer wires are connected to one another as they exit the layers, and the cathode layers are likewise connected together. In some embodiments, the wire connectors are gathered into corresponding wire bundles as they exit the layers, and the bundles can then be twisted together into a cable that can be laid in any direction to be routed through a feedthrough hole to terminal connections.

Other facets of the invention include various implantable medical devices, such as pacemakers, defibrillators, and cardioverters, incorporating one or more novel capacitors, as well as various methods of manufacture.

DETAILED DESCRIPTION

The following detailed description, which references and incorporates the figures, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

Figure 1:
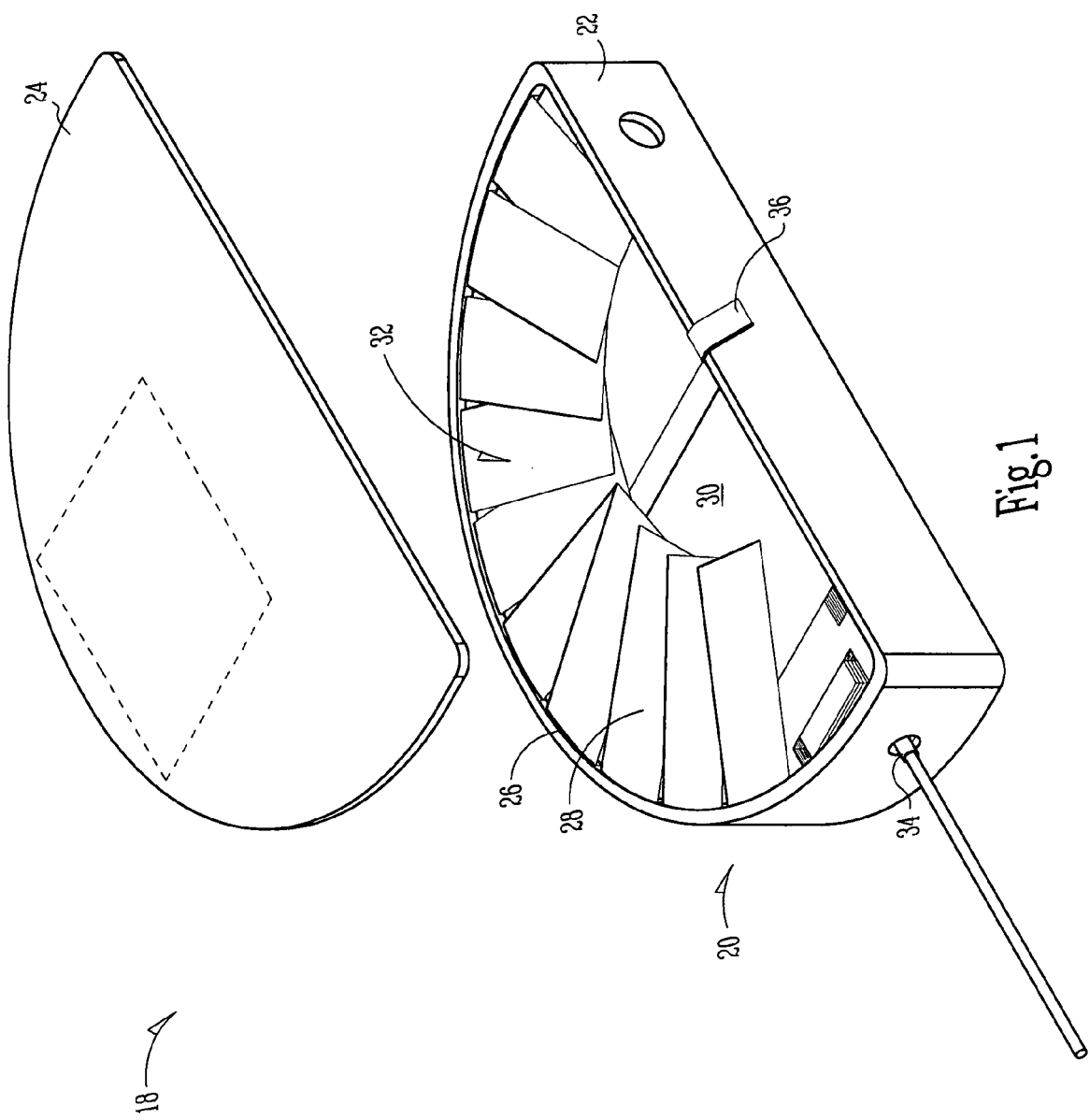
FIG. 1 is an exploded perspective view of a capacitor according to one embodiment of the present invention.

FIG. 1 shows a perspective view of a capacitor 18 according to one embodiment of the present invention. Capacitor 18 includes a capacitor container 20 including a case 22 and a lid, or cover 24 overlying case 22 for placement on an upper rim 26 of case 22. Although in one embodiment capacitor 18 has a D shape, other embodiments include square, oval, circular, rectangular and other symmetrical and asymmetrical shapes. A capacitor stack 28 with a top surface 30 is enclosed by container 20 which defines a chamber 32.

Capacitor stack 28 includes a plurality of cathode and anode foil layers separated by one or more separators. The anode foil layers are connected together and coupled to a feedthrough conductor 34. In one embodiment, feedthrough conductor 34 passes through a hole in case 22, and conductor 34 is electrically isolated from case 22.

The cathode foil layers of stack 28 are connected together and connected to a conductor 36. In one embodiment, cathode conductor 36 is a tab strip which is integral to one of the cathode layers. In other embodiments, cathode conductor 36 is a strip of aluminum tab stock connected to one or more of the cathode foil layers. Cathode conductor 36 provides an electrical connection between the cathode layers and case 22.

Figure 2:
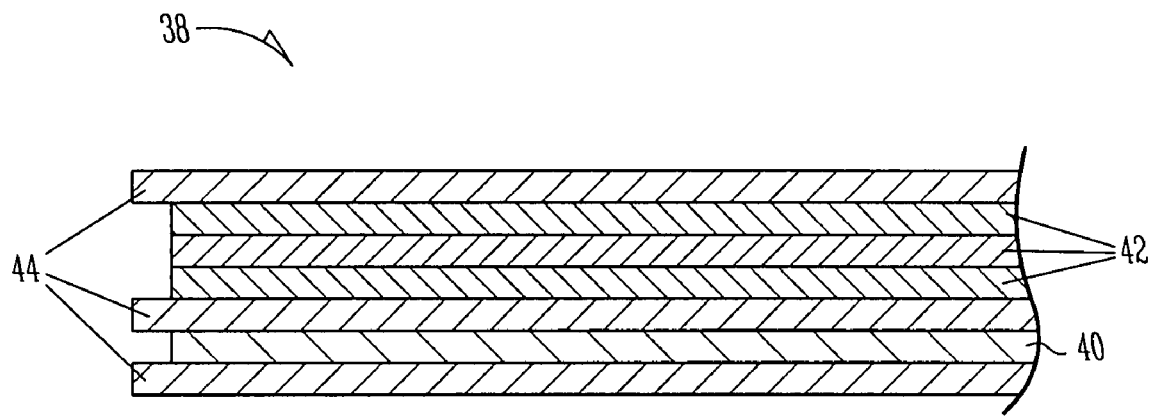
FIG. 2 is a cross sectional view of portions of the capacitive stack of FIG. 1.

FIG. 2 shows a capacitive element 38 in accord with one embodiment. Capacitor stack 28 includes a plurality of generally flat capacitive elements 38. Capacitive element 38 includes foil layers such as cathode layer 40 and anode layers 42 each of whose electrical elements are connected in parallel. In this embodiment, anode layers 42 form a triple anode structure. Other embodiments include single, double, triple, four, and/or more anode foils.

In one embodiment, the foil layers are etched and/or perforated. The number of capacitive elements determines the capacitance and thickness of the capacitor. Separators 44, such as two or more paper sheets, cover the opposite sides of the anode layer 42 as well as the opposite sides of cathode layer 40. At the periphery, the separators extend slightly beyond the cathode layer and the anode layers to prevent electrical shorting due to any misalignment.

Figure 3:
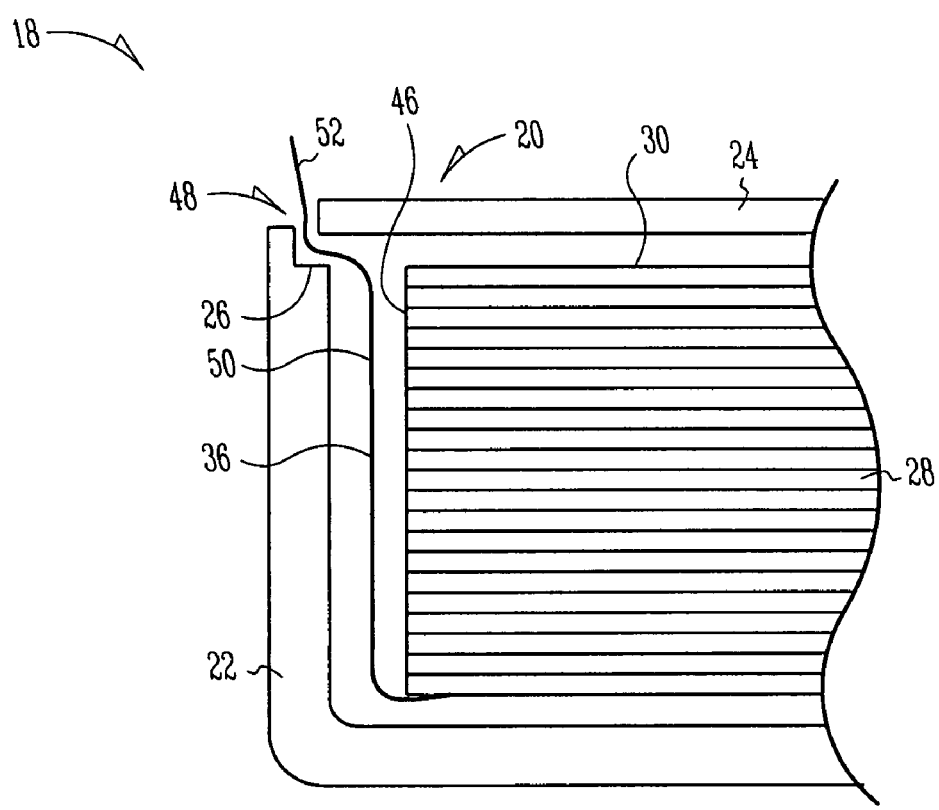
FIG. 3 is a partial cross sectional view of a capacitor with a cathode conductor positioned between the cover and the case according to one embodiment.
Figure 4:
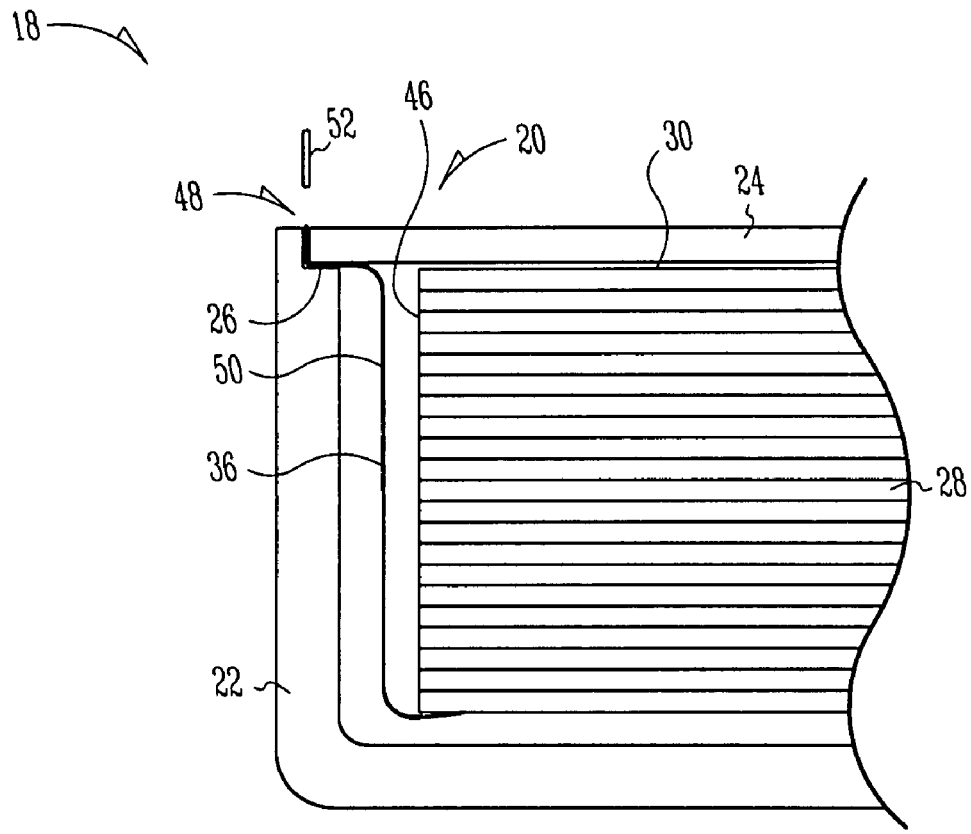
FIG. 4 is a partial cross sectional view of a capacitor with the cathode conductor attached to the cover and the case according to one embodiment.
Figure 5:
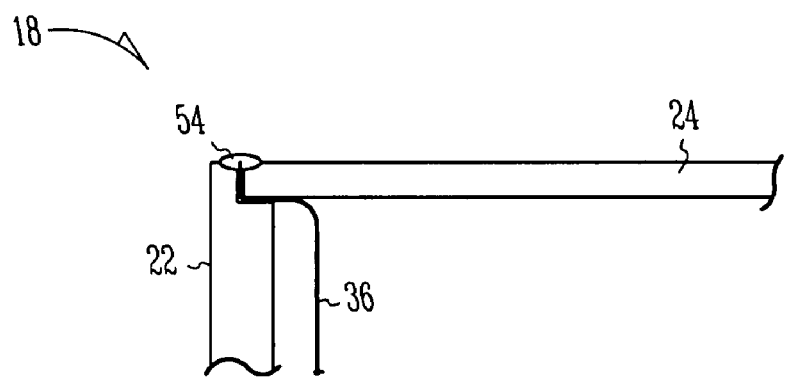
FIG. 5 is a partial cross sectional view of a capacitor with the cathode conductor welded to the cover and the case according to one embodiment.

FIGS. 3-5 show a partial cutaway view of capacitor 18 during respective manufacturing stages in accord with one or more embodiments of the present invention. Capacitor stack 28 includes top surface 30 and a lateral face 46 and includes one or more parallel connected capacitive elements, such as capacitive element 38 shown on FIG. 2. In one embodiment, the anodes of each capacitive element have respective tabs (not shown) compressed together and welded at their free ends, such as with a YAG laser. The welded tabs are then welded (or otherwise fastened or attached) to feedthrough conductor 34 that passes through case 22. (See FIG. 1). In some embodiments, an unetched, integral portion of each of one or more anodes is used to weld or attach the anode layers to one another.

In one embodiment, cathode tabs are attached or fastened to cathode conductor 36. As noted above, in some embodiments cathode conductor 36 is an integral extension of a cathode foil layer, meaning for example, that the cathode conductor and cathode foil layer are formed from a single piece of foil.

In one embodiment, cathode conductor 36 extends from capacitor stack 28 and is positioned and pinched between upper rim 26 of case 22 and cover 24. Cover 24 and case 22 form an interface or seam 48 at upper rim 26. Cathode conductor 36 is positioned in interface 48 between case 22 and cover 24. Cathode conductor 36 is pinched between case 22 and cover 24 defining an inner conductor portion 50 and an outer conductor portion 52. As shown in FIG. 4, in one embodiment, at least a portion of the outer conductor portion 52 is trimmed off of the cathode conductor 36.

In some embodiments, cathode conductor 36 is welded into place during the base/cover welding process, providing a mechanical and electrical connection to the case 22 without a separate connection procedure. In contrast, if the cathode conductor is connected to the case in a separate procedure, the extra connection requires that part of the capacitor stack be removed or the case be enlarged to allow space for routing and connecting the conductors, thereby reducing the packaging efficiency of the capacitor. The reduced packaging efficiency ultimately results in a larger capacitor. In some embodiments, conductor 36 is welded or otherwise fastened to the interior or exterior of cover 24 or to the exterior of case 22.

FIG. 5 shows a partial cutaway view of exemplary capacitor 18 with cover 24 welded to case 22. Cathode conductor 36 is positioned between case 22 and cover 24 at upper rim 26. Cathode conductor 36 is welded in the interface 48 between cover 24 and case 22, providing a mechanical and electrical connection to the container 20. The welded conductor 36, cover 24 and case 22 are welded together with a single bead 54. Optionally, the bead forms a hermetic seal between the cover 24 and case 22.

Among other advantages, one or more of the embodiments described above provide a capacitor structure which reduces the space required for connecting and routing the cathode conductor and thus allows a reduction in the size of the capacitor, or alternatively an increase in its energy storage capacity.

The embodiments described above show the cathode conductor electrically connected to the housing forming a cathodic housing. Alternative embodiments include positioning the anode conductor between the cover and case thereby connecting the anode layers and anode conductor to the housing forming an anodic housing.

An exemplary embodiment of a method to connect a cathode conductor to a capacitor housing is described below. The cathode conductor is connected to the housing by positioning the conductor between the case and the cover; positioning the cover on the case; and attaching the cover to the case so that the conductor is electrically and mechanically connected to the housing. In addition, other embodiments include positioning the conductor between the case and the cover at the upper rim and attaching the cover to the case at the upper rim. In one embodiment, the case and the cover form an interface and the positioning of the conductor between the case and the cover is in the interface. In another embodiment, the attaching the cover to the case comprises welding or soldering the cover to the case. The cathode conductor is welded into place using a single bead during the welding of the cover to the case, eliminating a separate step of connecting the cathode conductor to the case.

Figure 6:
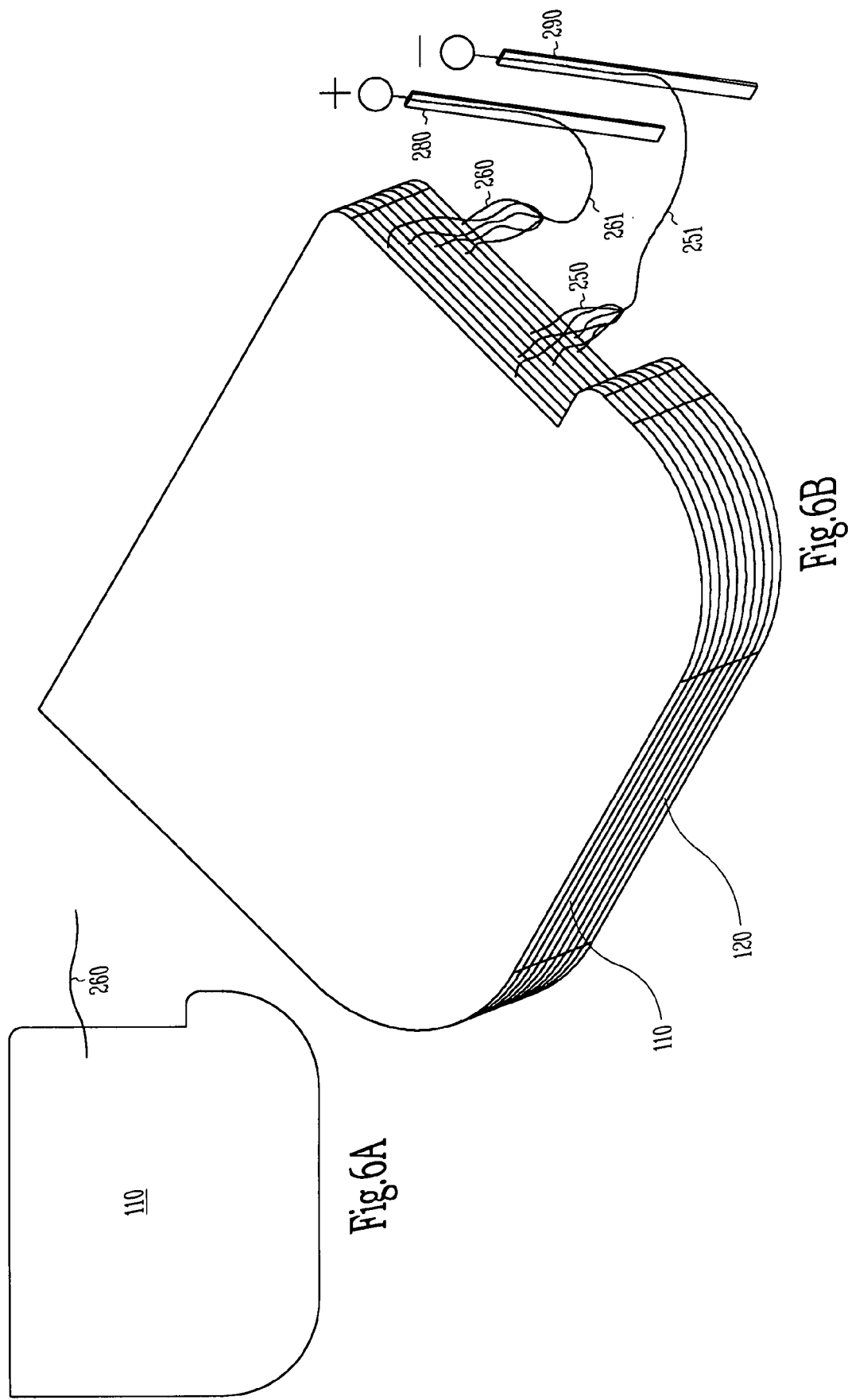
FIG. 6A is a view of a flat capacitor foil with an attached round wire connector according to one embodiment.
FIG. 6B is a perspective view of a flat capacitor showing round wire connectors for interconnecting anode and cathode plates.

FIG. 6A shows a top view of a foil connection according to one embodiment of the present invention. In this embodiment, a wire connector 260 is attached to a major surface of an anode layer 110 along a portion of the wire connector's length. In one embodiment, wire connectors are similarly connected to the cathode layers of the capacitor stack. In one embodiment, wire connector 250 is made of a high purity aluminum, and is a round wire and includes a diameter allowing the desired amount of bending and twisting as the connectors is routed through the capacitor case.

FIG. 6B shows a capacitor in accordance with one embodiment in which one or more round wire connectors 250 are connected to the cathode layers 120 and wire connectors 260 are connected to anode layers 110. The wire connectors may be made of high purity aluminum and are staked (or otherwise attached such as by welding, brazing, etc.) to the individual cathode and anode layers.

Wire connector 250 and 260 connect like types of layers together and can be used to connect the layers to external terminals. In the figure, the wires connected to the anode layers exit the layers at one common location while the cathode layer wires exit together at a different location. The anode layer wires 260 and cathode layer wires 250 are then gathered into corresponding wire bundles 261 and 251, respectively. The bundles can then be twisted together into a cable that can be laid in any direction to be routed through feedthroughs to terminal connections. In the figure, the anode layers 110 are electrically connected to positive terminal 280, and the cathode layers are electrically connected to negative terminal 290. By directly connecting the round wire connectors to the capacitor layers, there is no need for tabs that add to the space requirements of the capacitor case.

In one embodiment, wire connectors 250 and/or 260 are insulated with the insulation removed at the point of bundling in order to electrically connect like types of layers together. In another embodiment, the wires are uninsulated and routed through the case via an insulated feedthrough hole.

Advantageously, in one or more embodiments, the cathode and anode wires can be gathered into bundles and twisted into a cable that can be routed in any direction through a feedthrough of the capacitor case. This allows greater space efficiency and a smaller case for the capacitor.

Figure 7:
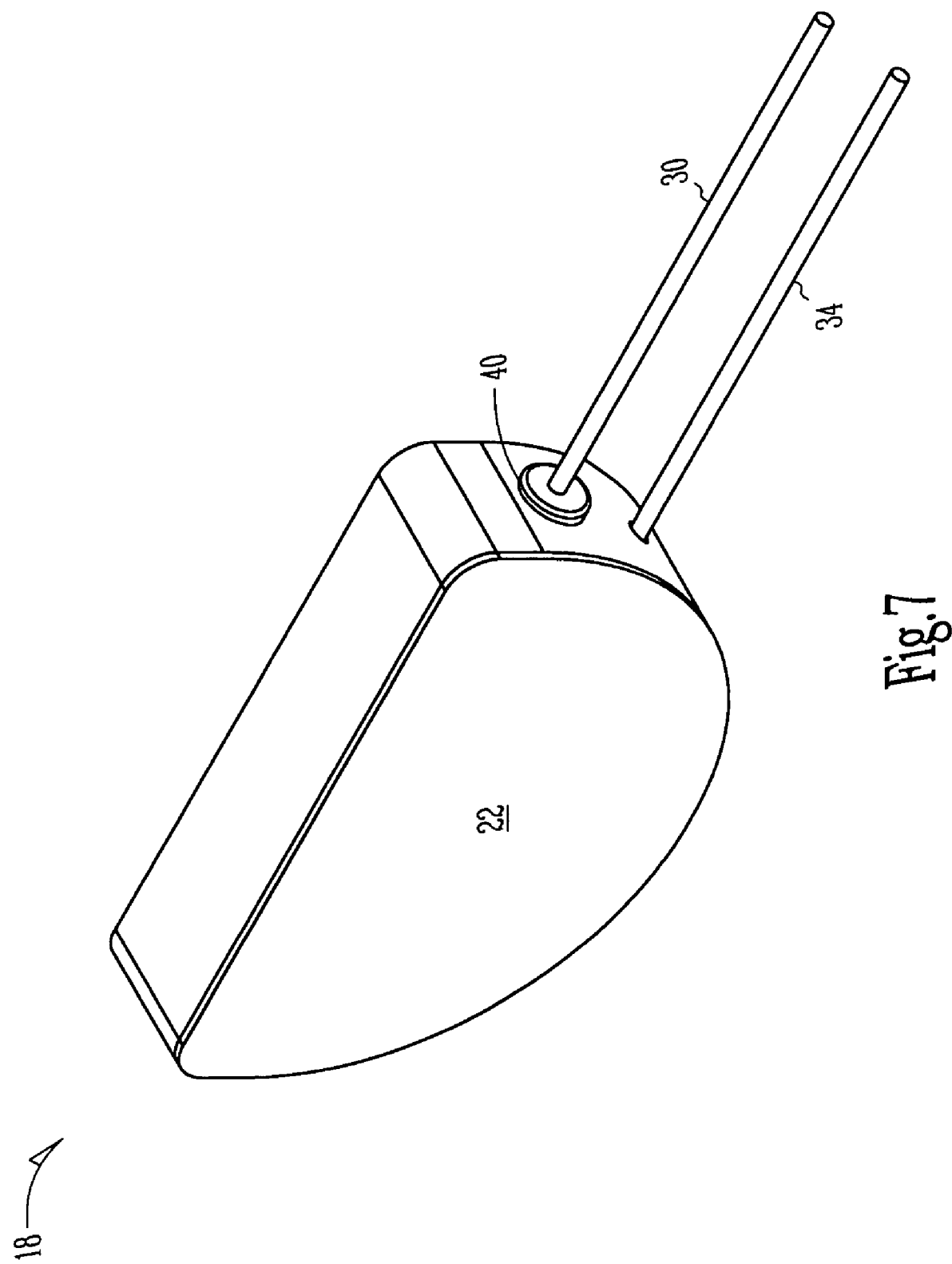
FIG. 7 is a view of a capacitor with an expanded end of a terminal wire attached to a case according to one embodiment.

FIG. 7 shows capacitor 18 having a terminal connection 30 in accord with one embodiment of the present invention. In this embodiment, feedthrough conductor 34 is attached to the anode layers inside the case as described above. The cathode layers are connected to the case in this embodiment, and terminal connector 30 is attached to the case in an end-on fashion by welding or brazing the end of the wire to the capacitor case.

In one embodiment, terminal connector 30 includes a body having an end surface which is substantially perpendicular to the body. The end surface is positioned so that the end surface is flushly positioned against the surface of the case and is butt-welded to the case, wherein terminal connector is only attached to the case at its end surface and not along any portions of its body.

In one embodiment, an expanded end 40 at the end of the wire is provided. The expanded end 40 in this embodiment is in the shape of a nailhead with a flat surface for attaching to the case. The surface area of the expanded end is sufficient to provide a securely welded connection while minimally altering the footprint of the capacitor case. The overall volume of the device housing can thus be reduced.

Figure 8A:
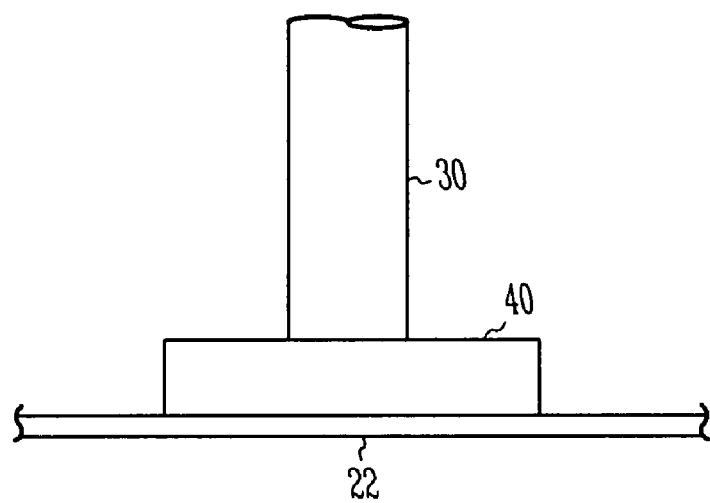
FIG. 8A is a later view of a terminal wire attached to a case according to one embodiment.

In FIG. 8A, terminal wire 30 with an expanded end 40 at its end is attached directly to a capacitor case 20 by, for example, arc percussive welding or laser welding.

Figure 8B:
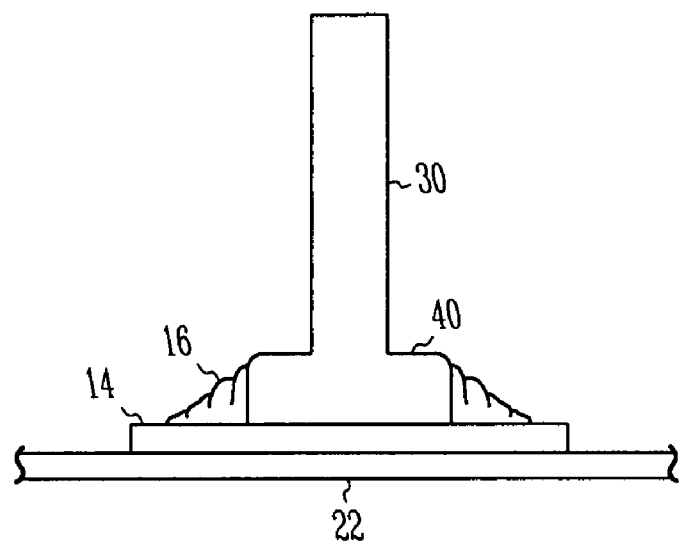
FIG. 8B is a later view of a terminal wire attached to a case according to one embodiment.

In FIG. 8B, expanded end 40 is attached with braze 16 to a piece of intermediate material 14 welded to the case 20. Both methods of attachment result in a low height profile that minimizes the amount of interconnect space required for connection of the capacitor to an external terminal.

In the capacitors described above, the case is electrically connected to the cathode layers to form a cathodic or negative case. In another embodiment of the invention, a terminal wire with an expanded end is attached to an anodic case which is formed by the case inner surface being electrically connected to the anode layers of the capacitor. Also, although the invention has been described above with reference to electrolytic capacitors, the invention may also be used in conjunction with other devices such as batteries or other types of capacitors such as wet tantalum capacitors. The term capacitor, as used herein, should be interpreted to include those devices as well.

Figure 9:
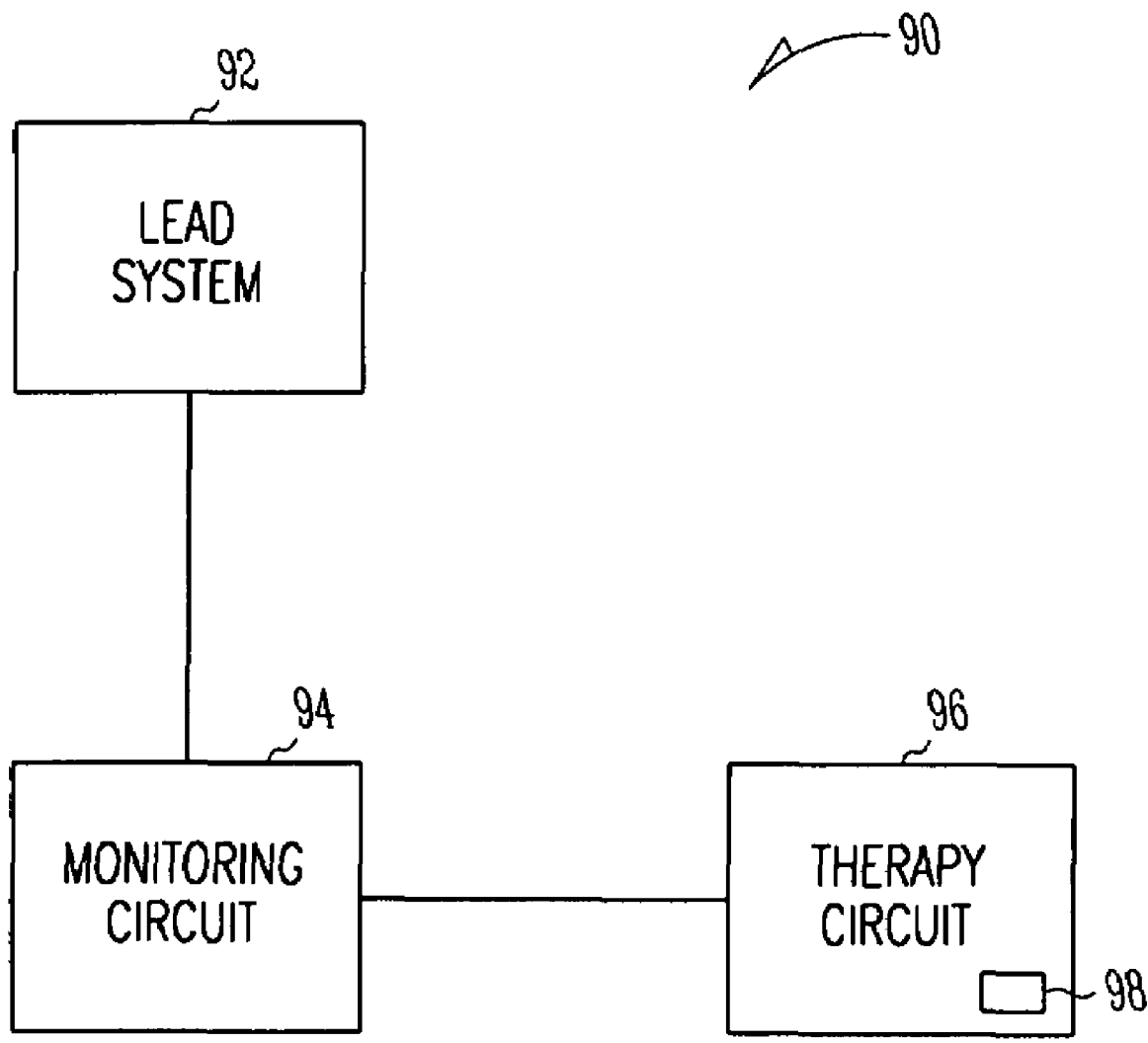
FIG. 9 is a schematic view of one embodiment of an implantable heart monitor having an energy storage component incorporating one or more capacitors in accordance with the invention.

FIG. 9 shows one of the many applications for capacitors incorporating one or more teachings of the present invention: an implantable medical device 90. As used herein, implantable medical device includes any implantable device for providing therapeutic stimulus to a heart muscle. Thus, for example, the term includes pacemakers, defibrillators, congestive heart failure devices, and cardioverters.

Device 90 includes a lead system 92, which after implantation electrically contact strategic portions of a patient's heart, a monitoring circuit 94 for monitoring heart activity through one or more of the leads of lead system 92, and a therapy circuit 96 which incorporates a capacitor 98 having one or more features of one or more embodiments of the capacitors described below.

In addition to implantable medical devices and other cardiac rhythm management devices, one or more teachings of the present invention can be incorporated into photographic flash equipment. Moreover, one or more features can be includes in cylindrical capacitors. Indeed, the teachings are pertinent to any application where high-energy, high-voltage, or space-efficient capacitors are desirable.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A capacitor comprising:
   a case;
   a capacitor stack; and
   a terminal wire;
   wherein, the capacitor stack is electrically and mechanically coupled to the case and wherein the terminal wire is attached to the case by attaching an end surface of the terminal wire to the case, wherein the end of the terminal wire is attached by brazing to a piece of intermediate material welded to the capacitor case.

2. The capacitor of claim 1 wherein the terminal wire has an expanded end for attaching to the case.

3. The capacitor of claim 2 wherein the expanded end of the terminal wire is in the shape of a nailhead.

4. The capacitor of claim 1 wherein the case is an electrically conductive case.

5. The capacitor of claim 1 wherein the terminal wire is connected to a cathodic case.

6. The capacitor of claim 1 wherein the terminal wire is connected to an anodic case.

7. A method for electrically connecting a terminal wire to a capacitor case comprising:
   positioning an end surface of the terminal wire flushly against a surface of the case;
   attaching only the end surface of the terminal wire to the case; and
   brazing the end of the terminal wire to a piece of intermediate material welded to the capacitor case.

8. The method of claim 7 wherein the end of the wire attached to the case is expanded.

9. The method of claim 7, wherein positioning the end surface includes positioning an expanded end surface of the terminal wire flushly against the outer surface of the case.

10. The method of claim 7, wherein the end surface of the terminal wire is in the shape of a nailhead.

11. The method of claim 7, wherein the capacitor case is a cathodic case.

12. The method of claim 11, wherein the capacitor case is an anodic case.

13. A capacitor comprising:
    a capacitor stack including a stack of flat capacitive elements with each element including a flat anode layer and a flat cathode layer with a separator interposed therebetween;
    a capacitor case including a feedthrough opening, wherein the capacitor stack is located within the case;
    a feedthrough terminal electrically coupled to one of the anode layer or the cathode layer, the feedthrough terminal extending through the feedthrough opening;
    wherein one of the anode layer or the cathode layer is electrically coupled to the capacitor case; and
    a terminal wire having an end surface flushly positioned against a surface of the capacitor case and attached to the capacitor case, wherein the end of the terminal wire is attached by brazing to a piece of intermediate material welded to the capacitor case.

14. The capacitor of claim 13 wherein the terminal wire has an expanded end for attaching to the case.

15. The capacitor of claim 14 wherein the expanded end of the terminal wire is in the shape of a nailhead.

16. The capacitor of claim 13, wherein the capacitor case is an electrically conductive case.

17. The capacitor of claim 13 wherein the terminal wire is connected to a cathodic case.

18. The capacitor of claim 13 wherein the terminal wire is connected to an anodic case.

\* \* \* \* \*

UNITED STATES PATENT AND TRADEMARK OFFICE
CERTIFICATE OF CORRECTION

PATENT NO.         : 7,576,973 B2                                      Page 1 of 1
APPLICATION NO.    : 11/904285
DATED              : August 18, 2009
INVENTOR(S)        : Brian L. Schmidt et al.

It is certified that error appears in the above-identified patent and that said Letters Patent is hereby corrected as shown below:

In column 7, line 15, in Claim 9, delete "the outer" and insert -- an outer --, therefor.

In column 7, line 20, in Claim 12, delete "claim 11," and insert -- claim 7, --, therefor.

Signed and Sealed this

Twelfth Day of January, 2010

David J. Kappos
*Director of the United States Patent and Trademark Office*